United States Patent [19]

Prior et al.

[11] Patent Number: 5,118,796
[45] Date of Patent: Jun. 2, 1992

[54] EFFICIENT LARGE-SCALE PURIFICATION OF IMMUNOGLOBULINS AND DERIVATIVES

[75] Inventors: Christopher P. Prior, Ballwin; Stephen A. Duffy, Florissant; Billy J. Moellering, St. Louis, all of Mo.

[73] Assignee: Centocor, Incorporated, Malvern, Pa.

[21] Appl. No.: 130,827

[22] Filed: Dec. 9, 1987

[51] Int. Cl.$^5$ .................. A61K 35/14; C07K 3/00; B01D 15/08
[52] U.S. Cl. .................. 530/388.1; 530/413; 530/416; 530/417; 530/418; 530/808; 530/830; 424/85.8; 210/635; 210/656
[58] Field of Search .............. 530/387, 388, 830, 808, 530/413, 416, 417, 418; 424/85.8; 210/635, 656

[56] References Cited

U.S. PATENT DOCUMENTS

| | | | |
|---|---|---|---|
| 3,664,994 | 5/1972 | Perper | 530/387 |
| 4,382,028 | 5/1983 | Paget | 424/85.8 |
| 4,606,825 | 8/1986 | Crane et al. | 210/635 |

OTHER PUBLICATIONS

Einarsson et al., *Biochimica Biophysica Acta* (1985) 830:1-10.
Randle et al., *J. Immunol. Methods* (1985) 77:25-36.
"Specific Monoclonal Antibody Purification Techniques", (1986) in *Separation News*, vol. 13.5, 7 pages of text.
"Q and S Sepharose Fast Flow" (1986) Pharmacia Data Sheet, 8 pages of text.
Sofer et al., *BioTechniques*, Nov./Dec. 1983, pp. 198-203.
Sofer, Bio/Technology, Dec. 1984, pp. 1035-1038.
*Pharmacia, Fine Chemicals*, Printed by Rahms i Lund, Mar. 1980-1, pp. 29-33.
Carlsson et al., "Purification of In Vitro Produced Mouse Monoclonal Antibodies. A Two-Step Procedure Utilizing Cation Exchange Chromatography and Gel Filtration", Journal of Immunological Methods, vol. 79, pp. 89-98, 1985.
Ostlund, "Large-Scale Purification of Monoclonal Antibodies", Trends in Biotechnology, vol. 11, pp. 288-292, 1986.
Saint-Blanchard et al. (1982) in Affinity Chromatography and Related Techniques (Elsevier Publishing Company, Amsterdam), pp. 305-312.
Scott et al., "Purification of Monoclonal Antibodies from Large-Scale Mammalian Cell Culture Perfusion Systems", Chemical Abstracts, vol. 107, Ref. No. 57407v, 1987.
Hasko et al., "Large-Scale Chromatographic Experiments for Plasma Fractionation", Chemical Abstracts, vol. 104, Ref. #95319p, 1986.
Takacs, "Characterization of Functional Fc Receptor Material from Human Lymphoblastoid Cell Lines. I. Large Scale Purification and Biochemical Analysis", Chemical Abstracts, vol. 94, Ref. #81950a, 1981.

Primary Examiner—Johnnie R. Brown
Assistant Examiner—Abdel A. Mohamed
Attorney, Agent, or Firm—Morrison & Foerster

[57] ABSTRACT

Improved methods for direct purification of product immunoglobulins or their derivatives from large volumes of mammalian cell culture medium include directly subjecting the cell culture medium to cation exchange treatment, so as to adsorb the product but not the contaminants. The eluted product is then recycled, or is applied to anion exchange, for further purification, and optionally subjected to additional steps. The product may be obtained in a form suitable for clinical applications, if desired.

19 Claims, 2 Drawing Sheets

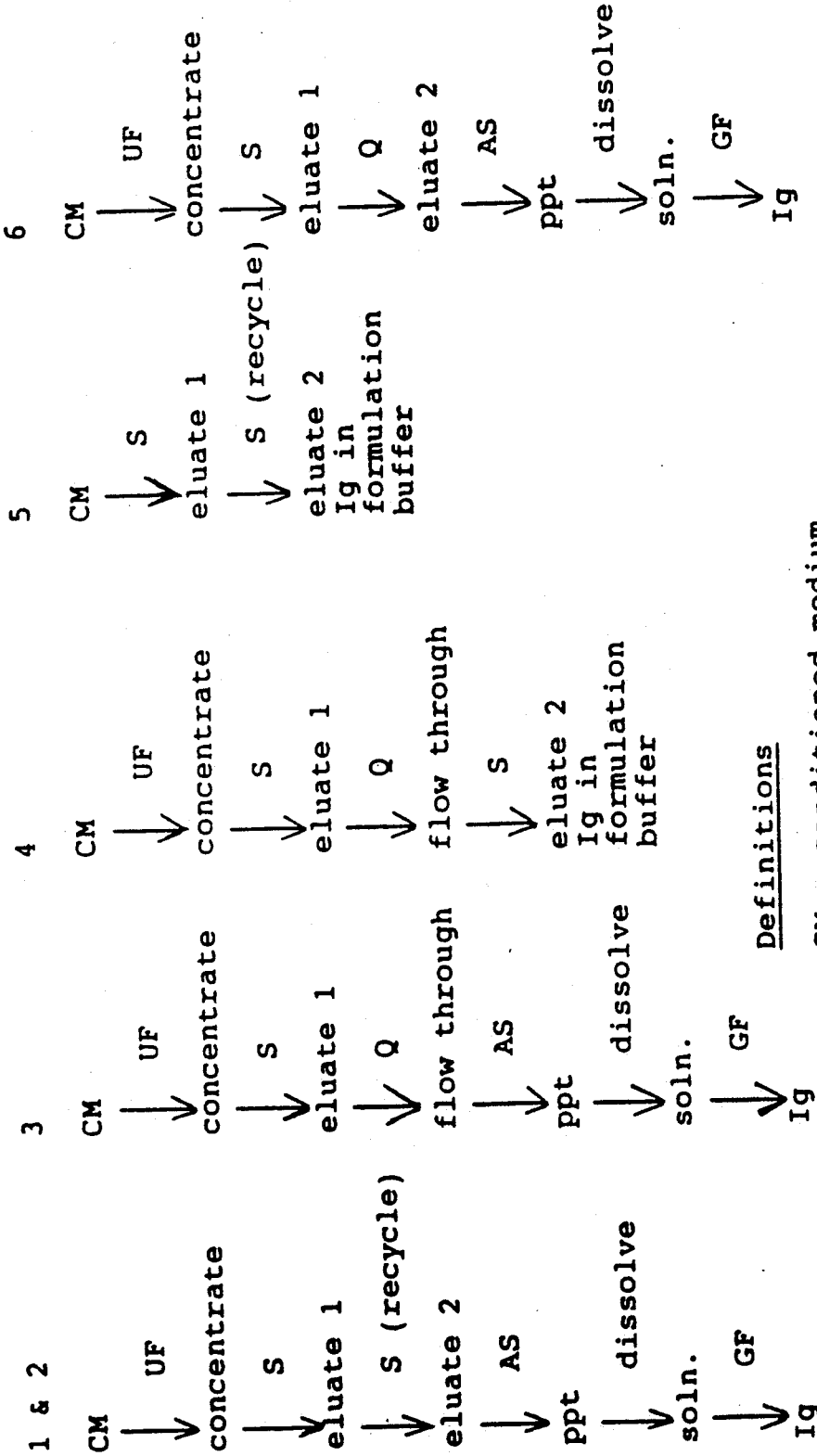

EFFICIENT LARGE-SCALE PURIFICATION OF IMMUNOGLOBULINS AND DERIVATIVES

TECHNICAL FIELD

The invention relates to methods to purify proteins produced by mammalian cells in media containing nutrient proteins. Specifically, the invention concerns methods to purify immunoglobulins or their derivatives from cell culture media containing serum proteins.

BACKGROUND ART

Production techniques for monoclonal antibodies generally fall into two categories: growth in ascites fluid and culture of immortalized cells secreting the antibodies in fermenters or cell culture chambers of various designs. For growth in cell culture, it is generally desirable to supply many nutrients in the form of animal sera as the growth of mammalian cells in defined media is difficult or impossible in most cases. As a result, desired protein products secreted by the cells into the medium are accompanied by large amounts of undesired serum proteins, and recovery in pure form of the desired product requires separation from these contaminants. Typically, the immunoglobulin molecules produced by hybridomas are present in the supernatants in the ug/ml range, whereas undesired proteins are present in approximately 1,000-fold greater concentrations. The availability of efficient tissue culture techniques has made possible the production of large quantities of antibodies on a scale involving volumes of hundreds or thousands of liters of culture medium. Techniques for recovery of the immunoglobulins on the mg-kg scale must take account of the necessity to deal with these large volumes, as well as the need to purify these materials away from serum proteins present in the nutrients.

A popular method for purification of some immunoglobulins from culture media has been the use of affinity chromatography, particularly affinity chromatography using protein-A, which has a general specific affinity for $F_c$ chains of certain IgG immunoglobulins. However, although this method is successful in achieving manyfold purification of the desired antibodies, the contaminants resulting directly from the materials used in the purification have been shown to have antigenic effects, and even when small in amount, they are potent in undesired bioactivity. Other disadvantages of the use of protein-A-based purification include the requirement for extreme pH conditions, the difficulty in "sanitizing" the adsorbent due to the lability of the protein-A, the inability of protein-A to bind certain IgG classes, and its failure to differentiate the desired antibody from the serum Ig in the medium. Also, if the procedure is used to purify antibodies for pharmaceutical use, the stipulation that the same resin cannot be reused for other product proteins is costly, due to the inherent cost of protein-A.

Typical methods for purifying immunoglobulins and their derivatives from cell culture medium include precipitation with salts followed by dialysis and anion exchange chromatography (Deutsch, H. F., et al, *Meth Immunol Immunochem* (1967), Vol. I, Academic Press, NY, p. 315); and high performance liquid chromatography (HPLC), Gemdic, M. J., et al, *Biotechniques* (1985) 3:378; Juarez-Salinas, H. S., ibid (1984) 2:164; Clezardin P., *J Chromatog* (1985) 319:67. Affinity chromatographic methods have been based on protein-A (Hjelm, H. K., *FEBS Lett* (1972) 28:73) and on anti-IgG antibodies (Yelton, D. C., et al, *Hybridoma* (1981) 1:5). The combination of gel filtration with cation exchange chromatography is discussed in Pharmacia's customer publication *Separation News* (1986) vol 13.5. All of these methods, while perhaps satisfactory on a laboratory scale, are totally unsuited to scaling to a high volume procedure for the production of kilogram levels of clinical grade antibodies.

The methods of the present invention are capable of providing immunoglobulins of >95% purity (wherein any remaining contaminants are benign) in a yield range of 40-75%, and in practical kilogram quantities from large volumes of culture supernatants. All of the processes employ direct contact of the concentrated or pH-adjusted medium with cation exchange resin under conditions wherein the important contaminants are not adsorbed.

DISCLOSURE OF THE INVENTION

The invention provides processes for obtaining substantial amounts of immunoglobulins in usable form from large volumes of culture media, in simple steps, to give product of high purity and high yield. Major segregation of the immunoglobulin product from contaminating medium materials, including nucleic acids, endotoxins and other proteins is achieved by direct contact of the medium with a cation exchange resin at low salt concentration, and at approximately pH 5-8, preferably about 6. Under these conditions, adsorption of the immunoglobulins results, but the majority of the contaminants, including most serum proteins in the medium, are not adsorbed. The immunoglobulins are then eluted, and the resulting eluate can be pH adjusted further purified by recycling through the same washed cation exchange column, under analogous conditions wherein it is readsorbed and reeluted. Alternatively, the eluate can be applied to an anion exchange column under conditions wherein the medium proteins are adsorbed but the immunoglobulins are not or the converse—i.e., wherein the immunoglobulin is selectively adsorbed. The resulting partially purified material may then be subjected to ammonium sulfate precipitation and gel filtration to yield the final product.

Thus, in one aspect, the invention is directed to a large-scale method to recover immunoglobulins or their derivatives from mammalian cell culture media that may contain high contaminant protein concentrations, which method comprises directly subjecting said media suitably adjusted for pH and salt concentration or concentrates (also suitably adjusted) thereof to treatment with a cation exchange resin, preferably fast-flow, under conditions wherein the product immunoglobulin or derivative is adsorbed and the majority of the medium contaminants are not.

In another aspect, the invention concerns a process for such purification wherein the product immunoglobulin eluted from the cation exchanger is subjected to an additional treatment with a cation exchange resin which can, if desired, be conducted by recycling the first eluate through the same column.

In still another aspect, the invention relates to a process wherein the eluate from the cation exchange column, whether recycled or not, is subjected to further purification steps; in particular, eluate from the cation exchange resin adsorption is subjected to treatment with an anion exchange resin under conditions wherein medium contaminants are adsorbed, but the product immunoglobulin is not, or, in the alternative, under conditions wherein the immunoglobulin is selectively adsorbed The recovered product immunoglobulin from any of these processes may be further purified, for example, by ammonium sulfate precipitation and gel filtration. However, alternate subsequent purification steps can also be used. These include, for example, subsequent further chromatographic purification such as an additional cation exchange step comprising elution in the final formulation buffer. Use of these alternate steps obviates the need for ammonium sulfate precipitation/gel filtration and is better suited for kilogram scale processes.

In another aspect, the invention is directed to the product immunoglobulin or derivatives thereof prepared by any of the process of the invention.

BRIEF DESCRIPTION OF THE DRAWINGS

FIG. 2 shows schematic summaries of Examples 1-6.

MODES OF CARRYING OUT THE INVENTION

A. Definitions

Figure 1:
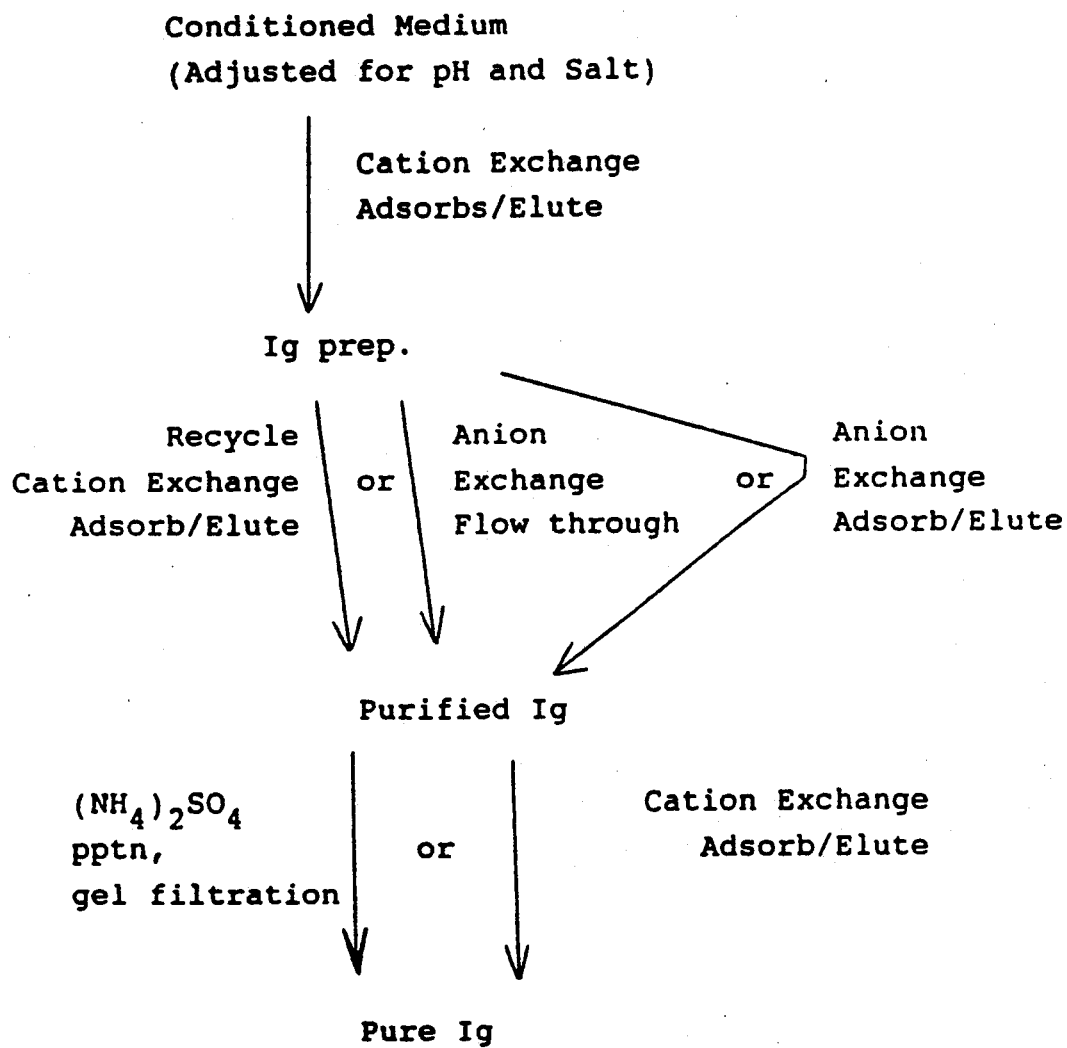
FIG. 1 shows a schematic of the processes of the invention.

As used herein, "immunoglobulin" is conventionally defined to mean the four-chain (two heavy, two light) glycosylated protein normally secreted by B cells of the immune system. As is understood, these proteins fall into several classes—IgG, IgA, IgE, and IgM. (IgM comprises further aggregates of the four-chain complex.) The "product" immunoglobulins to which the method of the invention is applied are monoclonal, i.e., they are secreted by immortalized forms of lymphocytes, usually hybridomas. These product immunoglobulins are usually prepared for their desired specificity, which specificity resides in the variable region of the protein. Therefore, certain derivatives of the product immunoglobulins are useful in providing this specificity, in particular F(ab')$_2$ fragments prepared by, for example, thiol-free papain digestion, Fab' fragments prepared by pepsin digestion and treatment with reducing agent, Fab fragments obtained by papain digestion, and so forth. The remaining regions of the antibody, for example, the F$_c$ regions of certain IgGs, are nonspecific, but have other utilities. These "derivatives" of the antibodies or immunoglobulins can also be purified from culture media using the method of the invention. Although, ordinarily, the intact product immunoglobulins will be first purified and then fragmented, it is also within the scope of the invention to generate the derivatives initially, and then subject these derivatives to the methods disclosed herein.

"Cation exchange resin" refers to any solid support in which the ligands covalently bound to the particulate support are negatively charged, and which thus has free cations for exchange with cations in a solution with which the resin is contacted. A wide variety of cation exchange supports, for example, those wherein the covalently bound groups are carboxylate or sulfonate, are known in the art. Of particular convenience in the methods of the invention are those which have large pore sizes, thus permitting a high flow rate. Among such commercially available resins are CMC-cellulose, Balcuband Abx, SP-Sephadex, and especially, Fast S-Sepharose (Pharmacia); however, the invention methods should not be considered to be limited to these. In general, useful supports include Sepharose, Sephadex, polyacrylamide, silica, and controlled pore glass, which contain covalently bound negatively charged ligands such as carboxylic or sulfonic acid moieties, offset by the cations available for exchange.

Conversely, anion exchange resins are based on the supports used also in cation exchange but conjugated to positively charged ligands, such as quaternary amino groups. Convenient commercially available anion exchange resins include DEAE cellulose, QAE Sephadex and Fast Q Sepharose (Pharmacia).

"Conditions wherein a subject protein (such as product immunoglobulin) is adsorbed/not adsorbed" refers to the pH and/or salt concentrations in aqueous solution which have the foregoing results, as the case may be. These conditions for a particular protein depend on its primary structure and, most specifically, on the number, type and distribution of acidic and basic amino acids residues included. In general, the protein will be positively charged at a pH below, and negatively charged at a pH above, its isoelectric point, i.e., the pH at which the protein is neutral. Under reasonable conditions of ionic strength, proteins with a net positive charge will be adsorbed to cation exchangers, and negatively charged proteins to anion exchangers. The precise conditions required for adsorption and elution depend on the nature of the resin protein and the buffer system and cannot therefore be described in general.

Particular advantage is taken herein of the difference between immunoglobulins and other serum proteins in their behavior with regard to adsorption to cation exchange resins. The major serum protein components such as albumin have isoelectric points below that characteristic of most antibodies and are not sufficiently positively charged at pH 5-8 to be adsorbed by the resin; however, the immunoglobulins are generally adsorbed under these conditions if salt concentration is sufficiently low.

In addition, most endotoxins and all nucleic acids are predominantly anions at neutral pH and at pH 5-8. They will therefore not be adsorbed to a cation exchange resin at that pH range due to electrostatic repulsion.

By "salt concentration" is meant ionic strength contributed by any salts, not necessarily limited to sodium chloride. Most of the buffers used in the preferred embodiments herein contain chloride, acetate, or phosphate salts especially the sodium salts. However, other ionic compounds could also be used, as long as the ionic strength generated by the composition is comparable to that exemplified. "Salt concentrations" are expressed herein as "equivalent to sodium chloride". This refers to a solution with an ionic strength which would be equal to that generated by the specified amount of sodium chloride. Thus, a solution having a "salt concentration equivalent to 10 mM sodium chloride" or just a "10 mM salt concentration" refers to a solution whose ionic strength is that generated by a 10 mM sodium chloride solution, regardless of whether this ionic strength is generated by sodium acetate, sodium phosphate, potassium acetate, potassium phosphate, or other salt.

"Contaminants" refers to materials in the cell culture media which are different from the desired immunoglobulin product. Typical contaminants include, importantly, nucleic acids, endotoxins, and serum-borne immunoglobulins. The method of the invention is particularly efficient in eliminating nucleic acid or endotoxin contaminants, since these materials re negatively charged at pH values where the desired immunoglobulins bear positive charges. In addition, as stated above, many serum proteins, in particular albumin, have isoelectric points which make their separation using ion exchange from the desired product immunoglobulins particularly advantageous.

With respect to serum immunoglobulins, these materials, also, are readily separated from the desired monoclonal antibody using this approach, since the conditions of adsorption can be fine-tuned to accommodate the particular characteristics of the desired homogeneous antibody preparation. This is in contrast, for example, to affinity purification using protein-A, which rests on an affinity for $F_c$-chains of certain IgGs, in general.

As used herein, "recycle", as it references recycling of the purified culture medium through ion exchange materials, refers to placing the eluted desired product in contact with the same resin from which it had been eluted under conditions where it can be readsorbed. It is then reeluted. Thus, in a typical embodiment, the same resin column is used. In the recycling, the resin from which the immunoglobulin has been eluted is reequilibrated, and the eluate is reapplied at a different pH. The salt conditions are then changed to those favoring elution, and the now even more highly purified material is reeluted.

"Directly", as it describes application of cell culture media to ion exchange resins refers to application of the medium to the resins without an intervening purification step. Adjustments may be made to the status of the medium prior to application to the resin, such as concentration to avoid the necessity of applying large volumes, dilution in order to lower salt concentration, pH adjustment, and the like. However, there are no intermediate purification steps to segregate the desired material from other proteins or contaminants in the medium, such as, for example, gel filtration, affinity chromatography, ammonium sulfate precipitation, and so forth.

B. General Description

Some general aspects of the problems encountered in large-scale purification, and a suggestion for the approaches claimed herein, are disclosed in Scott, R. W., et al, *Biotechnology Progress* (1987) 3:49-56, incorporated herein by reference.

The purification of product immunoglobulins from large volumes of culture medium rich in other proteins is greatly simplified by the initial removal of most contaminants, including proteins, nucleic acids and endotoxins, on exposure to an cation exchange resin, optimally through repeated treatment with such resin. While theoretically the supernatant could be directly subjected to the resin without prior concentration, because of the inconvenience of handling large volumes of fluid, it is preferable first to concentrate the medium to a workable volume. Alternatively, the pH and salt conditions of the medium can be directly adjusted, and can also be adjusted for the concentrate. Following concentration by ultrafiltration, for example, the salt concentration and pH of the resulting concentrate can be adjusted by diafiltration or by direct dilution to an ionic strength and pH which permits the adsorption of the product immunoglobulin or derivative onto the resin.

Concentration of large, e.g., 100, 1,000, or 10,000 liter volumes, can be achieved by commercially available processes, such as ultrafiltration. In this process, the medium is exposed to membranes which permit the passage of water molecules but do not permit larger substances to permeate. Systems for accomplishing this include cellulose triacetate membranes and polysulfone membranes. Cellulose triacetate membranes are preferred. Commercial membranes include those marketed by Amicon as a hollow fiber system, by Sartorius as a plate-and-frame system, and by Amicon or Millipore as spiral-wound cartridges. While these membranes have high putative molecular weight cutoff values, the pore sizes are, in fact, poorly defined, and furthermore polarization occurs at the surface. Therefore, cutoff values experienced in practice are, in fact, not precise, and the original salt concentration can be enhanced or maintained in the concentrated medium.

In the description below, it will be understood that conditions described for adsorption or nonadsorption or for elution of immunoglobulins to cation and anion exchange resins are illustrative for the sulfonic acid based cation exchange resin and quaternary ammonia-based anion exchange resin illustrated below. While these conditions may generally be extrapolated to alternative resins, they may not be precisely accurate for alternative ion exchangers, such as the carboxylic acid-based cation exchangers, for example, the carboxymethyl cellulose (CMC) resins or for the tertiary amine-based anion exchangers, illustrated by diethylaminoethyl cellulose (DEAE) resins commonly employed. Those of skill in the art will understand the modifications in conditions required to perform the method of the invention with alternative anion and cation exchange resins depending on the nature of the resin conjugated group which adsorbs the counter ion.

The concentrated medium is therefore either diluted with buffer or adjusted by diafiltration or dialysis to the appropriate salt concentration. For treatment with a typical cation exchange resin such as Fast S Sepharose, a salt concentration equivalent to approximately 10-40 mM, preferably 10 mM sodium chloride is required. The pH for adsorption is adjusted to pH 5-8, typically pH 6, and the concentrated medium is then contacted with a cation exchange resin, typically Fast S-Sepharose.

Alternatively, the medium may be adjusted without prior concentration to adjust pH and ionic strength before application to the cation exchange resin. As above, the pH can be adjusted by the addition of appropriate amounts of concentrated acid, base, or buffer, as needed, and salt adjustments can be made by direct dilution or, less conveniently, by diafiltration or dialysis.

Treatment with the cation exchange resin after appropriate pH and salt adjustment can be effected in a variety of ways, including batch treatment, but flow over a chromatography column is most convenient. The column is preequilibrated with a suitable buffer, also at the desired pH 5-8, typically pH 6, but at a higher salt concentration, for example approximately 30 mM, than that of the solution to be adsorbed. The conditions are such that the conductivity of the load is equal to or less than preferably equal to that of the equilibration buffer. Under these conditions, the product immunoglobulin is preferentially adsorbed onto the column, and the nucleic acids and endotoxins, which are anions at this pH, and most serum proteins, appear in the flow-through volume.

The product immunoglobulin is then eluted by raising the salt concentration to the equivalent of about 50-250 mM, preferably about 50 mM, sodium chloride, preferably using sodium acetate buffer, pH 5-8, typically pH 6, which has been adjusted for salt concentration with sodium chloride. The eluted immunoglobulin is then subjected to additional purification.

The next purification steps represent various aspects of this invention. In one aspect, the immediately following step comprises an additional cation exchange treatment step. This can be conducted with fresh cation exchanger, but it is more practical and preferred to employ reequilibration of the same cation exchange resin, and to recycle the first eluate through the regenerated cation exchange column. At least one additional treatment—i.e., recycling step is included, but three or four may be beneficial, depending on the nature of the preparation. Similar conditions wherein the immunoglobulin is adsorbed once again and reeluted are used, preferably using the regenerated resin from the first step on every pass.

In another aspect of the invention, the eluate is subjected to treatment by an anion exchange resin, under conditions wherein the remaining contaminants are adsorbed and the product immunoglobulin appears in the flow-through (nonadsorbed) volume. Since endotoxins and nucleic acids are anions under suitable conditions of pH, these materials are effectively removed. A preferred anion exchange resin is Fast-Q Sepharose. When equilibration and loading conditions of pH wherein the immunoglobulin does not behave as an anion are used with this resin, the desired immunoglobulins depending on the pI for the specific antibody, do not adsorb to the column. The precise conditions required depend on the specific antibody. The antibody will flow through the column when the pH is such that the antibody does not behave as an anion. (As antibodies are relatively large molecules with variations in surface charge, "behaves as" an anion is a more accurate description than "is" an anion.)

In still another aspect of the invention, the eluate is subjected to treatment by anion exchange resin under conditions which effect selective adsorption of the immunoglobulin. These conditions (for Fast-Q Sepharose) are pH values wherein the antibody behaves as an anion and salt concentrations usually less than 150 mM. The precise conditions for binding or nonbinding depend on the antibody, and these limits are very approximate. Binding will occur when the particular immunoglobulin "behaves as" an anion.

In either case, the thus further purified product solution may be subjected to additional steps. These may include precipitation in ammonium sulfate followed by gel filtration. The desired product fraction precipitates at approximately 300 g/l ammonium sulfate pH 7. The precipitate, when redissolved, can then be sized by gel filtration.

In lieu of, or in addition to, the ammonium sulfate precipitation/gel filtration steps, the immunoglobulins may be further purified by recycling them through an additional chromatographic step. For example, they may be again adsorbed to a cationic exchange resin under the conditions set forth above, and eluted in formulation buffer. This alternative procedure provides a more scalable process than does the ammonium sulfate precipitation/gel filtration sequence.

FIG. 1 shows a diagram of the processes encompassed by the invention. All of the procedures begin with conditioned medium which has been adjusted, if necessary, to obtain a suitable pH and salt concentration for the succeeding step involving cation exchange wherein the desired immunoglobulin is adsorbed and re-eluted to obtain an initial major purification. The conditioned medium may be concentrated before this step; however, this is not required. As set forth above, this direct cation exchange step employs loading conditions of pH 5-8 and salt concentrations of less than 50 mM; elution from the column is effected by increasing the salt concentration to a higher level, up to 250 mM. The elution is conveniently done by a single step adjustment of conditions; however, gradient elution could be employed if desired. This, however, is less suitable for commercial scale preparations.

As shown in the figure, the resulting immunoglobulin preparation can then be further purified using a number of alternatives. These alternatives include recycling through the cationic exchange resin to adsorb and reelute the immunoglobulin; treatment with an anion exchange resin under conditions which result in the immunoglobulin eluting in the flow-through volume—i.e., pH greater than 8 and salt concentrations greater than 100 mM or, in a third alternative, treatment with an anion exchange resin under conditions where the immunoglobulin is adsorbed—i.e., for Fast Q Sepharose, pH greater than 8 and a salt concentration equal to or greater than 100 mM. In any case, a further purified immunoglobulin preparation results. Of course, the "alternative steps" shown in FIG. 1 could also be employed sequentially in various combinations. Further purification may or may not be necessary; if desired, this can be effected either by ammonium sulfate precipitation followed by gel filtration, a method which is appropriate for smaller scale preparation, or can be effected by subsequent chromatography, exemplified in the figure by further cation exchange. Further purification through chromatographic procedures is preferred in large scale preparations; this has the additional advantage that the final elution step can often be conducted in formulation buffer, thus leading to a finished preparation.

Additional purification steps, of course, can be performed, such as gel electrophoresis, or alternative chromatographic methods. The outline in FIG. 1 is intended simply to show the required direct cation exchange step involved in the invention method, and the various alternative subsequent methods which are preferred.

It will be recognized that the approach of the invention offers a number of advantages over those traditionally used. In comparison to the use of protein-A as a primary purification step, for example, an immediately apparent advantage is that fragments continuing the variable regions can be purified using the method of the invention, whereas protein-A purification would be ineffective. This is due to the affinity of protein-A specifically for the $F_c$ regions of IgG immunoglobulins (other than IgG1). A further result of this specificity is the inability of protein-A affinity columns to purify immunoglobulins of other subclasses, such as IgA, IgE, or, more importantly, IgM. The high affinity for $F_c$ chains exhibited by protein-A also carries the disadvantage that it copurifies serum-contained IgG along with the desired monoclonal preparation. In short, the flexibility of cation exchange chromatography in permitting adjustment of conditions for appropriate adsorption of any particular desired monoclonal preparation offers inherent advantages over the affinity pattern of protein-A.

Another advantage offered by the use of ion exchange as a primary purification step is the ease with which the support can be "sanitized"—i.e., assured of being free of other impurities. Ion exchange resins can be washed with strong acids or bases to cleanse them of any undesired organic contaminants. On the other hand, protein-based affinity resins, including those using protein-A, cannot be subjected to such harsh treatment.

Related to this is the cost of the resin itself. Because anion and cation exchange resins are relatively inexpensive, they can be discarded, if necessary, as explained below, without any great increment in cost.

STATEMENT OF UTILITY

The purified immunoglobulin products of the invention are useful in a variety of contexts, and the products purified by the method of the invention can be any of hundreds of known monoclonal preparations. Included among monoclonal preparations for which the method of the invention is useful are monoclonal antibodies specific for T-cell receptors, such as the OKT series; antibodies specific for a variety of known proteins, such as the growth hormones, lymphokines, interferons, tissue plasminogen activator (tPA), urokinase, and the like; antibodies useful as diagnostics, such as those specific for human chorionic gonadotropin, LHRH, bacterial proteins, or viral coat proteins; and antibodies useful in therapy, such as those prepared against tumor antigens and optionally conjugated to toxins, and so forth. Particularly important is purification of antibodies individually prepared for therapeutic uses. For example, monoclonal antibodies generated against individual tumors will be needed in purified form so that they can be effectively administered to the subject.

For therapeutic antibodies, in particular, the methods of the invention offer an economic alternative to protein-A. Since because of regulatory requirements adsorbents cannot be reused to purify more than one product, the lower cost of cation (or anion) exchange resins as compared to protein-based affinity resins offers a clear cost saving. In addition, protein A-based resins appear to generate immunogenic substances which leach into the preparation and cause difficulty with obtaining purified product which is acceptable for pharmaceutical use.

EXAMPLES

The following examples are intended to illustrate but not to limit the invention. For convenience, all of the examples utilize a sulfonate-based cation exchanger, Fast S Sepharose and a quaternary amine-based anion exchanger, Fast Q Sepharose. The sequence of purification steps in Examples 1-6 is summarized in FIG. 2. As indicated in the figure, an initial concentrations step is optional, but in every case the medium is directly subjected to cation exchange to obtain an initial eluate containing the desired immunoglobulin. The initial eluate can then be recycled through this cation exchange resin, and then further purified by ammonium sulfate precipitation and gel filtration (Examples 1 and 2) or can be followed by treatment with anion exchange wherein the immunoglobulin elutes in the flow-through volume (Examples 3 and 4) and either further purified by ammonium sulfate precipitation and gel filtration (Example 3) or by further chromatography on cation exchange (Example 4). Example 5 results in a preparation of sufficient purity after a single recycling through cation exchange; Example 6 illustrates the use of adsorption to and elution from an anion exchange resin following the initial cation exchange step.

EXAMPLE 1

Purification of Anti-Parathyroid Immunoglobulin from Cultured Hybridoma Cells using Recycle Protocol on Cation Exchange Cultured medium from the murine hybridoma cell line BB5-G1, which secretes IgG1 specific for parathyroid hormone, described in U.S. Ser. No. 808,865, filed 13 Dec. 1985, and incorporated herein by reference, has a volume of 2,000 liters and an initial concentration of immunoglobulins of 10-20 ug/ml.

The recovered supernatant medium was concentrated 20-fold on a plate and frame ultrafiltration system with cellulose triacetate membranes (20,000 MW (nominal) cutoff). The concentrate was frozen at $-70°$ C. until further purification steps were conducted.

The frozen concentrate was thawed overnight at ambient temperature and diluted 1/10 (v/v) with buffer B (10 mM acetate buffer, pH 6.0). The diluted supernatant was passed over a 5 l S-Sepharose fast-flow bioprocess column (Pharmacia, 25.2 cm × 10 cm), which had been equilibrated with 5 column volumes of buffer A (20 mM sodium acetate, 10 mM NaCl, pH 6.0) at 300 ml/cm$^2$/h. The flow rate of the diluted supernatant was the same as the equilibration buffer. The column was washed with 5 column volumes of equilibration buffer, and then eluted with 4 column volumes of buffer C (20 mM sodium acetate, 30 mM NaCl, pH 6) at 60 ml/cm2/h.

The S-Sepharose resin was then regenerated using 1 M sodium chloride solution at 300 ml/cm$^2$/h and reequilibrated with 5 column volumes of buffer D (20 mM NaOAc, 30 mM NaCl, pH 5.5) at the same flow rate. The eluate from the original adsorption was adjusted to pH 5.5 with acetic acid and loaded onto the reequilibrated column at the same flow rate, and the adsorbed IgG1 was eluted with 3 column volumes of buffer E (20 mM NaOAc, 50 mM NaCl, pH 6.0) at a flow rate of 60 ml/cm$^2$/h.

The eluate was precipitated with ultrapure ammonium sulfate at 300 g/l, pH 7.2, allowing the slurry to sit at 4° C. for at least four hours. Precipitate was collected by centrifugation at 5,000 rpm for 30 min, washed by resuspending in 300 g/l ammonium sulfate solution. The washed pellet can be stored at $-70°$ C. Several pellets were thawed for 15 min at ambient temperature and dissolved with buffer F (phosphate-buffered saline, PBS) to a protein concentration of 25-30 mg/ml and clarified by centrifugation. The solution was then loaded onto a 10 l Sephacryl S-300 gel filtration bioprocess column (11.3 × 100 cm) (Pharmacia) previously equilibrated with buffer F. Fractions of 150 ml were collected and purity determined by SDS-PAGE. The antibody elutes at 40-50% column volume in fractions having more than 90% purity. Those fractions having more than 95% purity were pooled and frozen at $-70°$ C.

The percentage recovery of the steps in the foregoing process was determined by ELISA. The overall recovery measured after the concentration of the supernatant was 100%; after the first cycle on fast S-Sepharose, 75%; after the second cycle of fast S-Sepharose, 80%; and the overall recovery after the gel filtration step is 65%. Thus, the resulting IgG1 antibodies are recovered in 65% yield in greater than 95% purity.

The resulting immunoglobulin can be utilized as recovered, or may be fragmented into F(ab')2 fragments using thiol-free pepsin.

EXAMPLE 2

Purification of Monoclonal Antibodies from Cultured Hybridoma Cells using Recycle Protocol on Cation Exchange Conditioned medium from a hybridoma culture which secretes IgG2b antibodies was concentrated and treated as follows:

The medium was concentrated using a plate-and-frame ultrafiltration system employing cellulose triacetate membranes. Approximately 1200 liters of conditioned medium were concentrated 30-fold in three separate operations. The concentrates were stored at −70° C. until steps to purify the final product were initiated.

Each concentrate was processed separately. A frozen concentrate was thawed at 4° C., diluted 1 to 10 (v/v) with Buffer B (10 mM sodium phosphate, pH 6.4) to reduce the ionic strength and pH adjusted to 6.4 with dilute acetic acid. After diluting the concentrate was loaded onto a 5-liter S-Sepharose Fast Flow bioprocess column (Pharmacia, Inc.) that had been preequilibrated with approximately 5 column volumes of Buffer A (20 mM sodium phosphate, 10 mM sodium chloride, pH 6.4). The pH and conductivity of the diluted concentrate were such that the antibody selectively bound to the column while the bulk of the serum proteins and nonproteinaceous material were removed in the column flow-through. The column was then eluted with approximately 4 column volumes of Buffer C (20 mM sodium phosphate, 50 mM sodium chloride, pH 6.4). The antibody was eluted in a purified and concentrated form.

The S-Sepharose Fast Flow column was washed with 1 M NaCl prior to reequilibrating with approximately 5 column volumes of Buffer E (40 mM sodium acetate, 50 mM sodium chloride, pH 5.5). The purified antibody was then diluted 1 to 1 (v/v) with Buffer I (60 mM sodium acetate, pH 5.5), pH adjusted to 5.5 with dilute acetic acid and reloaded onto the column. The antibody was reeluted from the column by washing with approximately three column volumes of Buffer F (40 mM sodium acetate, 85 mM sodium chloride, pH 5.5).

The purified antibody was precipitated with 300 g/l ammonium sulfate (Buffer G) at 4° C. The precipitate was collected by centrifugation (5,000 rpm for approximately 10 minutes), resuspended in Buffer G, and recollected by centrifugation. The pellets were stored at −70° C. until further purified.

The ammonium sulfate pellets were thawed at 4° C. and resolubilized in a restricted volume of Buffer H (0.1 M sodium bicarbonate, pH 8.2) at a concentration of 15-20 mg/ml. The solution was applied to a 10 liter Sephacryl S-400 gel filtration column previously equilibrated with approximately two column volumes of Buffer H. Elution fractions (approximately 150 ml each) from the column were analyzed by SDS-PAGE and the fractions containing pure material (>95%) were pooled and stored. After the product from the last concentrate was purified, antibody obtained from each concentrate was pooled to form one lot of purified material. The concentration of purified antibody was approximately 5 mg/ml.

The pooled, purified antibody was concentrated in an Amicon stirred cell concentrator until a final concentration of 8-10 mg/ml was obtained. This concentration was performed at 4° C.

An SDS-polyacrylamide gel (10% acrylamide), run on the purified material under reducing conditions, shows two bands migrating in the heavy chain region (50-55 kd) and one band migrating in the light chain region (25 kd).

The two bands migrating in the heavy chain region were shown to be derived from the secreted IgG2b as follows. An Immuno-Blot transfer study showed that the two heavy chain bands cross-react with an anti-mouse probe with equal intensity. No cross-reactivity was observed with the negative control. A 10% SDS-polyacrylamide gel was run under reducing conditions using IgG2b untreated and IgG2b neuraminidase-treated (partially deglycosylated) antibodies. After deglycosylation, the 55 kd heavy chain migrates to the 50 kd position. These results confirm that the material migrating at the 50-55 kd position on the 10% SDS-polyacrylamide gel, run under reducing conditions, was from the purified IgG2b monoclonal antibody.

The overall recovery of the antibody from conditioned media to gel filtration was approximately 60% with a purity of greater than 95% as determined by SDS-PAGE.

EXAMPLE 3

Purification of Antibodies by Cation Exchange followed by Anion Flowthrough

Antibodies specific of class IgG2a were purified from culture medium as follows.

Concentration of the conditioned medium was performed using a plate-and-frame ultrafiltration system employing cellulose triacetate membranes. Approximately 2,086 liters of conditioned medium was concentrated 30-fold in five separate operations. The concentrates were stored at −70° C.

Each concentrate was thawed at 4° C. and purified separately through to the ammonium sulfate pellet. The concentrate was diluted 1:4 with buffer A (10 mM Tris, pH 7.0) to obtain a solution of pH 7.0. The pH and conductivity parameters of the buffer were defined such that the antibody selectively bound to a 5-liter column of Fast S Sepharose (Pharmacia Inc.) while the bulk of the serum proteins and nonproteinaceous material (e.g., nucleic acids, phospholipids, etc.) did not bind to the resin and fractionated in the column flow-through. Following a washing procedure to remove unbound serum protein remaining in the column, antibody was eluted by raising the sodium chloride concentration to 65 mM. The antibody was eluted in a concentrated and highly purified form.

The pH of the eluate was adjusted to 8.5, sodium chloride added to 0.1 M, and the solution was applied to the anion exchange resin, Fast Q Sepharose (Pharmacia Inc.). Under these conditions, further traces of contaminants were immobilized while the antibody was contained in the column flow-through.

The flow-through volume containing antibody was precipitated with ammonium sulfate (300 g/l) and stored as a centrifuged pellet at −70° C. The ammonium sulfate pellets derived from five separate batches were resolubilized to a protein concentration of 15-20 mg/ml in 0.1 M sodium phosphate, 0.15 M NaCl, pH 7.0, divided into equal samples, and applied to two separate gel filtration columns containing 10 liters of cross-linked Sephacryl 200(7) (Pharmacia Inc.).

Eluates from gel filtration columns were shown to be pure by analysis in SDS-PAGE and agarose isoelectric focusing.

EXAMPLE 4

Purification of IgG2a Monoclonal Antibodies by Cation Adsorption/Anion Flowthrough/Cation Adsorption Conditioned media containing IgG2a monoclonal antibodies were concentrated 30-fold using a plate and frame ultrafiltration system. Concentrates were stored at $-70°$ C. Each concentrate was thawed at 4° C. and diluted 1:3 (v:v) with 10 mM Tris pH 7.0. Diluted sample was loaded onto a 5 l Fast S Sepharose column pre-equilibrated with 20 mM Tris, 40 mM NaCl; pH 7.0, and the antibody was eluted with 20 mM Tris, 100 mM NaCl pH 8.0.

Solid sodium chloride was added at 0.5 g/l to the elution, the pH was adjusted to 8.7. The adjusted solution was loaded onto a 1 l Q Sepharose Fast Flow column which had been pre-equilibrated with 20 mM Tris, 100 mM NaCl; pH 8.7 and the antibody eluted in the column flow through volume.

The flow through was diluted 1:5 (v/v) with 10 mM $NaH_2PO_4$ pH 7.0 and loaded back onto a S Sepharose Fast Flow column after pre-equilibration with 10 mM $NaH_2PO_4$, 25 mM NaCl pH 7.0. The antibody adsorbed to the column was eluted in formulation buffer (PBS) at a concentration of 5 mg/ml.

EXAMPLE 5

Purification of IgM Antibodies by a Recycling Cation Exchange Protocol

Conditioned media containing IgM antibodies were pH adjusted to 5.5 with dilute acetic acid and loaded directly onto a 5 l Fast S Sepharose (Pharmacia) column which had been pre-equilibrated with Buffer A (40 mM NaOAc, 150 mM NaCl; pH 5.5) at 300 ml cm$^{-2}$ h$^{1}$. The antibody selectively bound to the resin, while the bulk of serum proteins were in the column flow through volume. The column was washed to remove additional serum proteins, and the antibody was eluted by raising the salt concentration to 250 mM. The antibody was eluted in a concentrated and purified form.

The S Sepharose Fast Flow column was washed with 1 M NaCl prior to re-equilibrating with 5 column volumes of Buffer B (20 mM Tris, 185 mM NaCl; pH 7.0). The purified antibody was then diluted 1 part eluted antibody to 0.4 parts buffer (v/v) with Buffer C (20 mM Tris, pH 7.0) pH adjusted to 7.0 with dilute sodium hydroxide and reloaded onto the column. The antibody was then eluted in a highly purified form with three column volumes of formulation buffer ($NaH_2PO_4$ 10 mM, NaCl 250 mM).

EXAMPLE 6

Purification of Antibodies using Cation Binding/Anion Binding

Conditioned media containing IgG antibodies were concentrated 30-fold using a plate and frame ultrafiltration system. Concentrates were stored at $-70°$ C. Each concentrate was thawed at 4° C. The concentrate was then diluted 1:10 (v/v) with 10 mM $NaH_2PO_4$, pH 6.5 and the diluted sample was loaded onto a 5 l Fast S Sepharose column equilibrated to 20 mM $NaH_2PO_4$, 10 mM NaCl pH 6.5. After washing, the IgG was then eluted with 20 mM $NaH_2PO_4$ + 125 mM NaCl, pH 6.5.

The eluate from the Fast S column was then diluted to a conductivity equal to 20 mM $NaH_2PO_4$ + 50 mM NaCl, pH 7.5 (approx. 1:2). The adjusted eluate was then loaded onto a Fast Q Sepharose column which had been preequilibrated to 20 mM $NaH_2PO_4$ + 50 mM NaCl. Under these conditions, the antibodies bind to the column. The IgG was then eluted with 20 mM $NaH_2PO_4$ + 100 mM NaCl, pH 7.5.

The IgG was precipitated from the eluate at 300 g/l ammonium sulfate. The precipitate was collected, dissolved in 1 M sodium phosphate, 0.15 M NaCl pH 7 at a protein concentration of 15-20 mg/ml, and passed through a Sephacryl 200 gel filtration column equilibrated with PBS.

We claim:

1. A method to purify product immunoglobulins or their derivatives from serum containing mammalian cell culture medium, which method comprises:

directly subjecting the cell culture medium, which is rich in other proteins, or a concentrated form thereof, to treatment with a cation exchange resin wherein the product immunoglobulin or derivative is adsorbed to the resin, and contaminants including said other proteins are not adsorbed; and recovering the adsorbed product from the resin in a first eluate, wherein the cation exchange resin is Fast S Sepharose and the conditions of adsorption are about pH 6-8 and about 10-40 mM salt concentration, and wherein the product is eluted at about pH 5-8 and approximately 50-250 mM salt.

2. The method of claim 1 wherein the culture medium is modified by the steps of concentrating said medium and adjusting to a salt concentration and pH effective to permit adsorption of product to said cation exchange resin prior to subjecting the medium to cation exchange.

3. The method of claim 2 wherein said step of concentrating said culture medium and step of adjusting the salt concentration and pH are conducted by ultrafiltration followed by dilution and addition of buffer.

4. The method of claim 1 wherein the culture medium directly subjected to treatment with a cation exchange resin is adjusted to a pH and salt concentration effective to permit adsorption of product to said cation exchange resin by dilution and addition of buffer.

5. The method of claim 1 which further includes subjecting the first eluate to an additional treatment with a cation exchange resin under conditions wherein the product immunoglobulin or derivative is adsorbed to the resin, and contaminants are not adsorbed; and recovering the adsorbed product from the resin in a second eluate.

6. The method of claim 5 wherein the additional treatment is conducted by recycling the first eluate at least once through the same reequilibrated resin to obtain a second eluate-containing product.

7. The method of claim 1 which further includes subjecting the first eluate to treatment with an anion exchange resin under conditions wherein the product is not adsorbed to the anion exchange resin to obtain a flow through preparation containing product.

8. The method of claim 1 which further includes subjecting the first eluate to treatment with an anion exchange resin under conditions wherein the product is adsorbed and then re-eluting from the anion exchange resin to obtain a second eluate-containing product.

9. The method of claim 1 which further includes a later step of precipitating the product with ammonium sulfate in a concentration effective to precipitate the product, and redissolving the precipitate.

10. The method of claim 5 which further includes a later step of precipitating the product with ammonium sulfate in a concentration effective to precipitate the product, and redissolving the precipitate.

11. The method of claim 7 which further includes a later step of precipitating the product with ammonium sulfate in a concentration effective to precipitate the product, and redissolving the precipitate.

12. The method of claim 8 which further later step of precipitating the product with sulfate in a concentration effective to precipitate the product, and redissolving the precipitate.

13. The method of claim 10 which further includes subjecting the redissolved product to gel filtration.

14. The method of claim 11 which further includes subjecting the redissolved product to gel filtration.

15. The method of claim 12 which further includes subjecting the redissolved product to gel filtration.

16. The method of claim 7 which further includes subjecting the flow-through preparation to an additional treatment with a cation exchange resin under conditions wherein the product immunoglobulin or derivative is adsorbed to the resin, and contaminants are not adsorbed; and recovering the adsorbed product from the resin in a second eluate.

17. The method of claim 8 which further includes subjecting the second eluate to an additional treatment with a cation exchange resin under conditions wherein the product immunoglobulin or derivative is adsorbed to the resin, and contaminants are not adsorbed; and recovering the adsorbed product from the resin in a third eluate.

18. The method of claim 1 wherein the medium initial volume of at least 1,000 liters.

19. The method of claim 1 wherein the product is an intact immunoglobulin.

* * * * *